United States Patent [19]

Uriarte

[11] 4,039,598

[45] Aug. 2, 1977

[54] PRODUCTION OF TETRABROMOBUTADIENE BY CATALYTIC OXYBROMINATION OF BUTANE

[75] Inventor: Anthony K. Uriarte, Pensacola, Fla.

[73] Assignee: Monsanto Company, St. Louis, Mo.

[21] Appl. No.: 716,420

[22] Filed: Aug. 23, 1976

[51] Int. Cl.² .............................................. C07C 21/20
[52] U.S. Cl. .............................. 260/655; 260/654 H; 260/662 R
[58] Field of Search ............... 260/654 H, 655, 659 R, 260/660, 662 R; 423/502

[56] References Cited

U.S. PATENT DOCUMENTS

| 2,381,037 | 8/1945 | Carter et al. | 260/655 |
| 3,214,481 | 10/1965 | Heineman et al. | 260/659 |
| 3,214,482 | 10/1965 | Caropresso et al. | 260/659 |
| 3,363,010 | 1/1968 | Schwarzenbek | 260/648 |
| 3,461,084 | 8/1969 | Li | 260/659 |
| 3,536,770 | 10/1970 | Skaperdas et al. | 260/659 |
| 3,546,306 | 12/1970 | McCarthy | 260/659 |
| 3,584,064 | 6/1971 | Weitz et al. | 260/654 H |

Primary Examiner—O. R. Vertiz
Assistant Examiner—Brian E. Hearn
Attorney, Agent, or Firm—Thomas Y. Awalt, Jr.

[57] ABSTRACT

1,1,4,4-Tetrabromobutadiene is produced by oxybrominating butane with free oxygen and bromine, the reaction being conducted in gaseous phase; and the butadiene is recovered by selective condensation of an effluent of the reaction medium.

10 Claims, No Drawings

PRODUCTION OF TETRABROMOBUTADIENE BY CATALYTIC OXYBROMINATION OF BUTANE

BACKGROUND OF THE INVENTION

A. Field of the Invention

The invention relates to the production of tetrabromobutadiene from butane.

B. The Prior Art

Tetrabromobutadiene, which has long been known as one of many organic intermediates (having functionality useful in the production of compounds based on one of the most common of the plentiful n-paraffinic compounds) has achieved more recent notability as a monomeric vehicle for incorporating bromine compounds into polymers for fire retardant purposes.

Heretofore, 1,1,4,4-/tetrabromobutadiene was prepared in a complex 2process involving intermediate purification and resulting in low selectivities and poor yields.

Oxychlorination has been employed for introducing functionality into olefinic hydrocarbons, but attempts to similarly activate paraffins have been much less successful due to the lack of selectivity obtained at reasonable conversion rates. Were it possible to oxyhalogenate n-butane with reasonably acceptable yields and rates of selectivity of the butadiene tetrahalide, such a process would be a significant advance in the art and is an object of this invention.

SUMMARY OF THE INVENTION

Butane is continously oxybrominated with free oxygen and bromine in the presence of a stabilized cupric bromide catalyst on a high surface area catalyst support comprising activiated alumina or silica by feeding the oxygen, bromine and butane in gaseous phase, at controlled rates and temperatures into a reactor maintained under conditions of pressure and temperature, the rates and conditions being preselected according to the particular apparatus, catalyst stabilizer and concentration of catalyst to form 1,1,4,4-tetrabromobutadiene in a reaction medium comprising oxygen, bromine and butane. The catalyst may be stabilized with potassium bromide, ammonium bromide, or a combination thereof. The product is isolated by selective condensation of an effluent of the reaction medium.

DESCRIPTION OF THE PREFERRED EMBODIMENTS

The butane which has been found to be suitable as the starting material in this reaction is normal butane.

I have discovered that when bromine, as opposed to the other halogens, is used under circumstances where an appropriate catalyst can be made stable enough to survive, oxyhalogenation of the n-butane can be successfully employed in the preparation of a brominated butadiene, offering distinct advantages over the expensive and impractical prior art processes.

I have also found that if a stabilized cupric bromide catalyst is presented to the oxybromination reaction on a high surface area support comprising activated alumina and/or silica, the reaction can easily be made to favor the 1,1,4,4-tetrabromobutadiene. Presently known examples of activated alumina or silica which are suitable for supporting the reaction include: gamma alumina ($\gamma$-$Al_2O_3$), and all high surface area silicates including aluminum derivatives of silicates such as $Al_2O_3 \cdot SiO_2$. Surprisingly, no other metal classes of catalyst supports have been found which will favor this particular reaction. High surface area supports are those in which the surface area is in excess of about 100 $m^2$/g. Presently manufactured catalyst supports run from about 5 to about 350 $m^2$/g.

Stabilization of the cupric bromide catalyst is achieved by presenting it to the reaction mixed wtih a relatively small amount of a potassium or ammonium halide. Maintance of staility of the catalyst is essential, and (for oxybromination of butane to tetrbromobutadiene) no other method of maintaining such stability than by the use of these particular compounds as part of the catalyst mixture has yet been found. Salts of the alkaline metals other than potassium do not satisfactorily maintain stability of the cupric halide. While the amount of stabilizing salt if not critical, satisfactory results have been achieved employing stabilizing salts in the amount of 23-50% of the total weight of the catalyst mixture.

In a preferred preparation of the catalyst for presentation, the cupric halide and the potassium or ammonium halide is dissolved in a suitable solvent which is used to saturate the catalyst support, subsequently to be removed by filtration and/or evaporation as appropriate, the support then being dried under a nitrogen flow at about 150° C. to leave a catalyst mixture concentration of about 5-10% by weight based on the catalyst support. Solvents known to be suitable for catalyst preparation as described are water and methanol.

Depending upon the particular apparatus, catalyst concentration, choice of stabilizer and feed rate of various components, a variety of conditions of pressure and temperature may be selected which will satisfctorily produce the tetrabromobutadiene at yields and rates of selectivity far in excess of those known to be reported in the prior art. The vapor phase reaction is preferably carried out in a fluid or fixed bed single-stage reactor at temperatures above 250° C. and below about 300° C. at atmospheric pressure. I have found that excessive cracking and charring of the reactants in the products will occur when the reaction is conducted at temperatures in excess of 300° C.

In order to avoid unreacted bromine and to prevent over-bromination an excess of the butane over the bromine and the oxygen should be employed, preferably by way of a mole feed ratio of oxygen and bromine to that of the butane of about 0.2–0.6 and 0.1–0.5, respectively. The feeding gases are preferably but not necessarily diluted with nitrogen so as to achieve the above-described desirable mole feed ratios, and to avoid the flammability region for the butane which is about 1.8–49 and 1.9–8.5 mole percent butane in oxygen and air, respecitvely. Of course the feed rates of the various components should be individually adjusted so as to provide maximum selectivity of the desired product with respect to the particular apparatus employed, catalyst concentration, stabilizer choice and concentration, pressure and temperature.

Any effective selective condensation method may be employed to recover the brominated butadiene. Preferred is a 3-stage condensation which may be operated at successively decreasing temperatures.

EXAMPLES

The reactor was a 2 × 50 cm Pyrex tube to which a gas inlet manifold preheater was attached. A fluidized sand bath was employed to maintain the temperature of the reactor and preheater. A series of condenser traps were provided to accept the effluent of the reactor.

These traps were adjusted to provide a first condensation temperature of 25° C., a second at 0° C., and a third at −78° C. The catalyst support in each example (as described) was impregnated with cupric bromide and potasium bromide in the amounts indicated. Temperatures of the reactor and feed rates of the gases contact time and product analysis are as shown in the following table:

TABLE I

| Example No. | Catalyst Composition | Temp. ° C. | Res. Time Sec. | Gas Feed Rates at 25° C. & 1 atm | | | | Product Mole % |
|---|---|---|---|---|---|---|---|---|
| | | | | $C_4H_{10}$ | $Br_2$ | $O_2$ | $N_2$ | 1,1,4,4-tetra bromobudadiene |
| 1 | 15% $CuBr_2$ + 10% KBr on γ-alumina (Girdler T-126) 3/16 inch pellets surface area 300 m²/g | 250 | 5.1 | 100 | 23 | 50 | 400 | 90 |
| 2 | 10% $CuBr_2$ + 3% KBr on γ-alumina 80-200 mesh Harshaw Al-1401P surface area 180 m²/g | 290 | 1.7 | 100 | 24 | 50 | 400 | 85 |
| 3 | 20% $CuBr_2$ + 12% KBr on silica (α-quartz) Girdler T-1571 3/16 inch spheres surface area 130 m²/g | 250 | 5.1 | 100 | 23 | 50 | 400 | 90 |
| 4 | 15% $CuBr_2$ + 10% KBr on Silica alumina surface area 100 m²/g 3/16 inch pellets Girdler T-1219 | 270 | 4.9 | 100 | 24 | 50 | 400 | 60 |

I claim:

1. The process for the production of 1,1,4,4-tetrabromobutadiene comprising continuously oxybrominting butane with free oxygen and bromine in the presence of a cupric bromide catalyst stabiized with a member of the group consisting of a potassium or ammonium halide on a high surface area support comprising a member of the group consisting of activated alumina, and silica by feeding the oxygen, bromine and butane, in gaseous phase, at controlled rates and temperatures into a reactor maintained under conditions of pressure and temperature to form 1,1,4,4-tetrabromobutadiene and selectively condensing an effluent of the reaction medium thereby to recover the 1,1,4,4-tetrabromobutadiene.

2. The process of claim 1 wherein the catalyst is stabilized with a member of the group consisting of potassium bromide and ammonium bromide.

3. The process of Claim 1 wherein the catalyst is supported by gamma alumina which is impregnated with 5–15% by weight of stabilized cupric bromide.

4. The process of claim 1 wherein the mole feed ratio of oxygen to butane is 0.2–0.6.

5. The process of claim 1 wherein the mole feed ratio of bromine to butane is 0.1–0.5.

6. The process of claim 1 wherein the selected condensation of an effluent of the reaction medium is conducted at a temperature of at least 25° C.

7. The process of claim 1 wherein the reaction is conducted at atmospheric pressure at a temperature of 250°–300°40 C.

8. The process of claim 1 wherein the butane is fed at about 100 ml/min, the oxygen at about 50 ml/min, the bromine at about 23–24 ml/min, and the temperature of the feeding gases is about 25° C.

9. The process of claim 1 wherein the feeding gases also include about 400 ml/min of nitrogen at 25° C.

10. The process of claim 9 wherein reaction time is 1.7–5.1 seconds.

* * * * *